(12) United States Patent
Morrissey

(10) Patent No.: US 7,579,024 B2
(45) Date of Patent: Aug. 25, 2009

(54) COMPOSITIONS FOR ENHANCING IMMUNE FUNCTION

(75) Inventor: Edward Stephen Morrissey, Ojai, CA (US)

(73) Assignee: Botanica BioScience Corp., Ojai, CA (US)

( * ) Notice: Subject to any disclaimer, the term of this patent is extended or adjusted under 35 U.S.C. 154(b) by 0 days.

(21) Appl. No.: 11/973,631

(22) Filed: Oct. 9, 2007

(65) Prior Publication Data

US 2008/0089961 A1    Apr. 17, 2008

Related U.S. Application Data

(60) Provisional application No. 60/828,455, filed on Oct. 6, 2006.

(51) Int. Cl.
*A61K 36/00* (2006.01)
(52) U.S. Cl. .................. 424/725; 424/769; 424/774; 424/778
(58) Field of Classification Search .................. None
See application file for complete search history.

(56) References Cited

U.S. PATENT DOCUMENTS

2007/0160696 A1 *   7/2007   Clymer et al. .............. 424/756

OTHER PUBLICATIONS

DW ACC 2004-488510, Apr. 2004, Derwent, Huang.*
DW ACC 1981-46280D, Jun. 1981, Derwent, Hashimoto et al.*

* cited by examiner

*Primary Examiner*—Christopher R Tate
*Assistant Examiner*—Randall Winston
(74) *Attorney, Agent, or Firm*—McKinney Law Group; Jeffrey A. McKinney

(57) ABSTRACT

The present invention is directed to compositions for enhancing immune function that include ingredients from natural sources. It is further directed to methods of administering the compositions and kits containing the compositions. In a composition aspect, the composition is for regulating immune function. It consists essentially of: 2 weight percent to 95 weight percent *Eleuthero;* 2 weight percent to 95 weight percent *Stephania;* and, 2 weight percent to 95 weight percent *Epimedium.*

9 Claims, No Drawings

COMPOSITIONS FOR ENHANCING IMMUNE FUNCTION

PRIORITY CLAIM

This application claims the benefit of U.S. Provisional Application No. 60/828,455, which was filed Oct. 6, 2006, under 35 U.S.C. § 119, which is hereby incorporated-by-reference for all purposes.

FIELD OF THE INVENTION

The present invention is directed to compositions for enhancing immune function, methods of administering the compositions and kits containing the compositions. It is specifically directed to compositions that include ingredients from natural sources.

BACKGROUND OF THE INVENTION

A seven ingredient, immune support formula was developed. The formula was shown to aid in the reduction of cold and flu symptoms, as well as reduce the duration of a cold or the flu. The ingredients of the formula are as follows: *Astragalus* root; Asian ginseng root; *Echinacea purpurea*; *Angelica sinensis* root; *Eleuthero* root; *Stephania* root; and, *Epimedium* aerial parts.

*Astragalus* was the primary ingredient in the formula and one responsible for many of the observed benefits. The other ingredients were thought to play a supporting role in the composition.

While the *astragalus* formulation affords desirable outcomes with respect to cold and flu prevention and/or suppression, it is rather large in volume and relatively expensive to make. It is accordingly an object of the present invention to provide a more compact, less expensive immune support formula that exhibits beneficial effects against colds and flu.

SUMMARY OF THE INVENTION

The present invention is directed to compositions for enhancing immune function that include ingredients from natural sources. It is further directed to methods of administering the compositions and kits containing the compositions.

In a composition aspect, a composition for regulating immune function is provided. The composition consists essentially of: 2 weight percent to 95 weight percent *Eleuthero*; 2 weight percent to 95 weight percent *Stephania*; and, 2 weight percent to 95 weight percent *Epimedium*.

In a method aspect, a method for treating a cold is provided. The method includes the following steps: administration of a composition, and wherein the composition consists essentially of: 2 weight percent to 95 weight percent *Eleuthero*; 2 weight percent to 95 weight percent *Stephania*; and, 2 weight percent to 95 weight percent *Epimedium*.

In a kit aspect, a kit for the prevention or alleviation of symptoms related to a cold is provided. The kit includes: a container; a composition consisting essentially of 2 weight percent to 95 weight percent *Eleuthero*, 2 weight percent to 95 weight percent *Stephania*, and, 2 weight percent to 95 weight percent *Epimedium*; and, a set of instructions related to the administration of the composition.

DETAILED DESCRIPTION OF THE INVENTION

The present invention is directed to compositions for enhancing immune function that include ingredients from natural sources. It is further directed to methods of administering the compositions and kits containing the compositions.

Compositions

The compositions of the present invention include *Eleuthero*, *Stephani* and *Epimedium* as active ingredients in various ratios. Typically, the composition comprises *Eleuthero* (2-95 wt. %), *Stephania* (2-95 wt. %), and *Epimedium* (2-95 wt. %) as active ingredients. Nonlimiting examples of ratios of active ingredients embodied in compositions are provided below:

*Eleuthero* (95 wt. %); *Stephania* (2 wt. %); and, *Epimedium* (3 wt. %);

*Eleuthero* (95 wt. %); *Stephania* (3 wt. %); and, *Epimedium* (2 wt. %);

*Eleuthero* (90 wt. %); *Stephania* (5 wt. %); and, *Epimedium* (5 wt. %);

*Eleuthero* (85 wt. %); *Stephania* (5 wt. %); and, *Epimedium* (10 wt. %);

*Eleuthero* (85 wt. %); *Stephania* (10 wt. %); and, *Epimedium* (5 wt. %);

*Eleuthero* (80 wt. %); *Stephania* (10 wt. %); and, *Epimedium* (10 wt. %);

*Eleuthero* (75 wt. %); *Stephania* (10 wt. %); and *Epimedium* (15 wt. %);

*Eleuthero* (75 wt. %); *Stephania* (15 wt. %); and *Epimedium* (10 wt. %);

*Eleuthero* (70 wt. %); *Stephania* (20 wt. %); and *Epimedium* (10 wt. %);

*Eleuthero* (70 wt. %); *Stephania* (15 wt. %); and *Epimedium* (15 wt. %);

*Eleuthero* (70 wt. %); *Stephania* (10 wt. %); and *Epimedium* (20 wt. %);

*Eleuthero* (65 wt. %); *Stephania* (25 wt. %); and *Epimedium* (10 wt. %);

*Eleuthero* (65 wt. %); *Stephania* (20 wt. %); and *Epimedium* (15 wt. %);

*Eleuthero* (65 wt. %); *Stephania* (15 wt. %); and *Epimedium* (20 wt. %);

*Eleuthero* (65 wt. %); *Stephania* (10 wt. %); and *Epimedium* (25 wt. %);

*Eleuthero* (60 wt. %); *Stephania* (30 wt. %); and *Epimedium* (10 wt. %);

*Eleuthero* (60 wt. %); *Stephania* (25 wt. %); and *Epimedium* (15 wt. %);

*Eleuthero* (60 wt. %); *Stephania* (20 wt. %); and *Epimedium* (20 wt. %);

*Eleuthero* (60 wt. %); *Stephania* (15 wt. %); and *Epimedium* (25 wt. %);

*Eleuthero* (60 wt. %); *Stephania* (10 wt. %); and *Epimedium* (30 wt. %);

*Eleuthero* (55 wt. %); *Stephania* (35 wt. %); and, *Epimedium* (10 wt. %);

*Eleuthero* (55 wt. %); *Stephania* (30 wt. %); and, *Epimedium* (15 wt. %);

*Eleuthero* (55 wt. %); *Stephania* (25 wt. %); and, *Epimedium* (20 wt. %);

*Eleuthero* (55 wt. %); *Stephania* (20 wt. %); and, *Epimedium* (25 wt. %);

*Eleuthero* (55 wt. %); *Stephania* (15 wt. %); and, *Epimedium* (30 wt. %);

*Eleuthero* (55 wt. %); *Stephania* (10 wt. %); and, *Epimedium* (35 wt. %);

*Eleuthero* (50 wt. %); *Stephania* (40 wt. %); and, *Epimedium* (10 wt. %);

*Eleuthero* (50 wt. %); *Stephania* (35 wt. %); and, *Epimedium* (15 wt. %);

*Eleuthero* (50 wt. %); *Stephania* (30 wt. %); and, *Epimedium* (20 wt. %);

*Eleuthero* (50 wt. %); *Stephania* (25 wt. %); and, *Epimedium* (25 wt. %);
*Eleuthero* (50 wt. %); *Stephania* (20 wt. %); and, *Epimedium* (30 wt. %);
*Eleuthero* (50 wt. %); *Stephania* (15 wt. %); and, *Epimedium* (35 wt. %);
*Eleuthero* (50 wt. %); *Stephania* (10 wt. %); and, *Epimedium* (40 wt. %);
*Eleuthero* (45 wt. %); *Stephania* (45 wt. %); and, *Epimedium* (10 wt. %);
*Eleuthero* (45 wt. %); *Stephania* (40 wt. %); and, *Epimedium* (15 wt. %);
*Eleuthero* (45 wt. %); *Stephania* (35 wt. %); and, *Epimedium* (20 wt. %);
*Eleuthero* (45 wt. %); *Stephania* (30 wt. %); and, *Epimedium* (25 wt. %);
*Eleuthero* (45 wt. %); *Stephania* (25 wt. %); and, *Epimedium* (30 wt. %);
*Eleuthero* (45 wt. %); *Stephania* (20 wt. %); and, *Epimedium* (35 wt. %);
*Eleuthero* (45 wt. %); *Stephania* (15 wt. %); and, *Epimedium* (40 wt. %);
*Eleuthero* (45 wt. %); *Stephania* (10 wt. %); and, *Epimedium* (45 wt. %);
*Eleuthero* (40 wt. %); *Stephania* (50 wt. %); and, *Epimedium* (10 wt. %);
*Eleuthero* (40 wt. %); *Stephania* (45 wt. %); and, *Epimedium* (15 wt. %);
*Eleuthero* (40 wt. %); *Stephania* (40 wt. %); and, *Epimedium* (20 wt. %);
*Eleuthero* (40 wt. %); *Stephania* (35 wt. %); and, *Epimedium* (25 wt. %);
*Eleuthero* (40 wt. %); *Stephania* (30 wt. %); and, *Epimedium* (30 wt. %);
*Eleuthero* (40 wt. %); *Stephania* (25 wt. %); and, *Epimedium* (35 wt. %);
*Eleuthero* (40 wt. %); *Stephania* (20 wt. %); and, *Epimedium* (40 wt. %);
*Eleuthero* (40 wt. %); *Stephania* (15 wt. %); and, *Epimedium* (45 wt. %);
*Eleuthero* (40 wt. %); *Stephania* (10 wt. %); and, *Epimedium* (50 wt. %);
*Eleuthero* (35 wt. %); *Stephania* (55 wt. %); and, *Epimedium* (10 wt. %);
*Eleuthero* (35 wt. %); *Stephania* (50 wt. %); and, *Epimedium* (15 wt. %);
*Eleuthero* (35 wt. %); *Stephania* (45 wt. %); and, *Epimedium* (20 wt. %);
*Eleuthero* (35 wt. %); *Stephania* (40 wt. %); and, *Epimedium* (25 wt. %);
*Eleuthero* (35 wt. %); *Stephania* (35 wt. %); and, *Epimedium* (30 wt. %);
*Eleuthero* (35 wt. %); *Stephania* (30 wt. %); and, *Epimedium* (35 wt. %);
*Eleuthero* (35 wt. %); *Stephania* (25 wt. %); and, *Epimedium* (40 wt. %);
*Eleuthero* (35 wt. %); *Stephania* (20 wt. %); and, *Epimedium* (45 wt. %);
*Eleuthero* (35 wt. %); *Stephania* (15 wt. %); and, *Epimedium* (50 wt. %);
*Eleuthero* (35 wt. %); *Stephania* (10 wt. %); and, *Epimedium* (55 wt. %);
*Eleuthero* (30 wt. %); *Stephania* (60 wt. %); and, *Epimedium* (10 wt. %);
*Eleuthero* (30 wt. %); *Stephania* (55 wt. %); and, *Epimedium* (15 wt. %);
*Eleuthero* (30 wt. %); *Stephania* (50 wt. %); and, *Epimedium* (20 wt. %);
*Eleuthero* (30 wt. %); *Stephania* (45 wt. %); and, *Epimedium* (25 wt. %);
*Eleuthero* (30 wt. %); *Stephania* (40 wt. %); and, *Epimedium* (30 wt. %);
*Eleuthero* (30 wt. %); *Stephania* (35 wt. %); and, *Epimedium* (35 wt. %);
*Eleuthero* (30 wt. %); *Stephania* (30 wt. %); and, *Epimedium* (40 wt. %);
*Eleuthero* (30 wt. %); *Stephania* (25 wt. %); and, *Epimedium* (45 wt. %);
*Eleuthero* (30 wt. %); *Stephania* (20 wt. %); and, *Epimedium* (50 wt. %);
*Eleuthero* (30 wt. %); *Stephania* (15 wt. %); and, *Epimedium* (55 wt. %);
*Eleuthero* (30 wt. %); *Stephania* (10 wt. %); and, *Epimedium* (60 wt. %);
*Eleuthero* (25 wt. %); *Stephania* (65 wt. %); and, *Epimedium* (10 wt. %);
*Eleuthero* (25 wt. %); *Stephania* (60 wt. %); and, *Epimedium* (15 wt. %);
*Eleuthero* (25 wt. %); *Stephania* (55 wt. %); and, *Epimedium* (20 wt. %);
*Eleuthero* (25 wt. %); *Stephania* (50 wt. %); and, *Epimedium* (25 wt. %);
*Eleuthero* (25 wt. %); *Stephania* (45 wt. %); and, *Epimedium* (30 wt. %);
*Eleuthero* (25 wt. %); *Stephania* (40 wt. %); and, *Epimedium* (35 wt. %);
*Eleuthero* (25 wt. %); *Stephania* (35 wt. %); and, *Epimedium* (40 wt. %);
*Eleuthero* (25 wt. %); *Stephania* (30 wt. %); and, *Epimedium* (45 wt. %);
*Eleuthero* (25 wt. %); *Stephania* (25 wt. %); and, *Epimedium* (50 wt. %);
*Eleuthero* (25 wt. %); *Stephania* (20 wt. %); and, *Epimedium* (55 wt. %);
*Eleuthero* (25 wt. %); *Stephania* (15 wt. %); and, *Epimedium* (60 wt. %j;
*Eleuthero* (25 wt. %); *Stephania* (10 wt. %); and, *Epimedium* (65 wt. %);
*Eleuthero* (20 wt. %); *Stephania* (70 wt. %); and, *Epimedium* (10 wt. %);
*Eleuthero* (20 wt. %); *Stephania* (65 wt. %); and, *Epimedium* (15 wt. %);
*Eleuthero* (20 wt. %); *Stephania* (60 wt. %); and, *Epimedium* (20 wt. %);
*Eleuthero* (20 wt. %); *Stephania* (55 wt. %); and, *Epimedium* (25 wt. %);
*Eleuthero* (20 wt. %); *Stephania* (50 wt. %); and, *Epimedium* (30 wt. %);
*Eleuthero* (20 wt. %); *Stephania* (45 wt. %); and, *Epimedium* (35 wt. %);
*Eleuthero* (20 wt. %); *Stephania* (40 wt. %); and, *Epimedium* (40 wt. %);
*Eleuthero* (20 wt. %); *Stephania* (35 wt. %); and, *Epimedium* (45 wt. %);
*Eleuthero* (20 wt. %); *Stephania* (30 wt. %); and, *Epimedium* (50 wt. %);
*Eleuthero* (20 wt. %); *Stephania* (25 wt. %); and, *Epimedium* (55 wt. %);
*Eleuthero* (20 wt. %); *Stephania* (20 wt. %); and, *Epimedium* (60 wt. %);
*Eleuthero* (20 wt. %); *Stephania* (15 wt. %); and, *Epimedium* (65 wt. %);

*Eleuthero* (20 wt. %); *Stephania* (10 wt. %); and, *Epimedium* (70 wt. %);
*Eleuthero* (15 wt. %); *Stephania* (75 wt. %); and, *Epimedium* (10 wt. %);
*Eleuthero* (15 wt. %); *Stephania* (70 wt. %); and, *Epimedium* (15 wt. %);
*Eleuthero* (15 wt. %); *Stephania* (65 wt. %); and, *Epimedium* (20 wt. %);
*Eleuthero* (15 wt. %); *Stephania* (60 wt. %); and, *Epimedium* (25 wt. %);
*Eleuthero* (15 wt. %); *Stephania* (55 wt. %); and, *Epimedium* (30 wt. %);
*Eleuthero* (15 wt. %); *Stephania* (50 wt. %); and, *Epimedium* (35 wt. %);
*Eleuthero* (15 wt. %); *Stephania* (45 wt. %); and, *Epimedium* (40 wt. %);
*Eleuthero* (15 wt. %); *Stephania* (40 wt. %); and, *Epimedium* (45 wt. %);
*Eleuthero* (15 wt. %); *Stephania* (35 wt. %); and, *Epimedium* (50 wt. %);
*Eleuthero* (15 wt. %); *Stephania* (30 wt. %); and, *Epimedium* (55 wt. %);
*Eleuthero* (15 wt. %); *Stephania* (25 wt. %); and, *Epimedium* (60 wt. %);
*Eleuthero* (15 wt. %); *Stephania* (20 wt. %); and, *Epimedium* (65 wt. %);
*Eleuthero* (15 wt. %); *Stephania* (15 wt. %); and, *Epimedium* (70 wt. %);
*Eleuthero* (15 wt. %); *Stephania* (10 wt. %); and, *Epimedium* (75 wt. %);
*Eleuthero* (2 wt. %); *Stephania* (95 wt. %); and, *Epimedium* (3 wt. %);
*Eleuthero* (3 wt. %); *Stephania* (95 wt. %); and, *Epimedium* (2 wt. %);
*Eleuthero* (5 wt. %); *Stephania* (90 wt. %); and, *Epimedium* (5 wt. %);
*Eleuthero* (5 wt. %); *Stephania* (85 wt. %); and, *Epimedium* (10 wt. %);
*Eleuthero* (10 wt. %); *Stephania* (85 wt. %); and, *Epimedium* (5 wt. %);
*Eleuthero* (10 wt. %); *Stephania* (80 wt. %); and, *Epimedium* (10 wt. %);
*Eleuthero* (10 wt. %); *Stephania* (75 wt. %); and, *Epimedium* (15 wt. %);
*Eleuthero* (10 wt. %); *Stephania* (70 wt. %); and, *Epimedium* (20 wt. %);
*Eleuthero* (10 wt. %); *Stephania* (65 wt. %); and, *Epimedium* (25 wt. %);
*Eleuthero* (10 wt. %); *Stephania* (60 wt. %); and, *Epimedium* (30 wt. %);
*Eleuthero* (10 wt. %); *Stephania* (55 wt. %); and, *Epimedium* (35 wt. %);
*Eleuthero* (10 wt. %); *Stephania* (50 wt. %); and, *Epimedium* (40 wt. %);
*Eleuthero* (10 wt. %); *Stephania* (45 wt. %); and, *Epimedium* (45 wt. %);
*Eleuthero* (10 wt. %); *Stephania* (40 wt. %); and, *Epimedium* (50 wt. %);
*Eleuthero* (10 wt. %); *Stephania* (35 wt. %); and, *Epimedium* (55 wt. %);
*Eleuthero* (10 wt. %); *Stephania* (30 wt. %); and, *Epimedium* (60 wt. %);
*Eleuthero* (10 wt. %); *Stephania* (25 wt. %); and, *Epimedium* (65 wt. %);
*Eleuthero* (10 wt. %); *Stephania* (20 wt. %); and, *Epimedium* (70 wt. %);
*Eleuthero* (10 wt. %); *Stephania* (15 wt. %); and, *Epimedium* (75 wt. %);
*Eleuthero* (10 wt. %); *Stephania* (10 wt. %); and, *Epimedium* (80 wt. %).
*Eleuthero* (10 wt. %); *Stephania* (5 wt. %); and, *Epimedium* (85 wt. %);
*Eleuthero* (5 wt. %); *Stephania* (10 wt. %); and, *Epimedium* (85 wt. %);
*Eleuthero* (5 wt. %); *Stephania* (5 wt. %); and, *Epimedium* (90 wt. %);
*Eleuthero* (3 wt. %); *Stephania* (2 wt. %); and, *Epimedium* (95 wt. %);
*Eleuthero* (2 wt. %); *Stephania* (3 wt. %); and, *Epimedium* (95 wt. %);

Compositions of the present invention may take different forms, depending on the exact formulation employed. Non-limiting examples include:

Into capsules with the addition of flour, starch, modified starch, maltodextrin, cellulose, modified cellulose, protein hydrolysate, rice powder, whey powder, calcium phosphate, calcium carbonate, lactose, saccharides, sorbitol, mannitol, xylitol, stearic acid, stearate, silica, silicate, polyethylene glycol, flavors, and/or colors, among others.

Into tablets with the addition of starch, modified starch, maltodextrin, cellulose, methylcellulose, ethylcellulose, hydroxypropylmethylcellulose, modified cellulose, protein hydrolysate, rice powder, whey powder, calcium phosphate, calcium carbonate, lactose, sweeteners (e.g. sucrose, fructose, glucose, corn syrup, saccharides, saccharine, sucralose, aspartame, etc.), sorbitol, mannitol, xylitol, (gum tragacanth, gum arabic, agar, guar gum, locust bean gum, karaya gum, xanthan gum, etc.) zein, saccharides, stearic acid, stearate, silica, silicate, polyethylene glycol, pharmaceutical glaze, wax, flavors, and/or colors, among others.

Into powdered drink mix with the addition of starch, modified starch, maltodextrin, cellulose, modified cellulose, protein hydrolysate, whey powder, calcium phosphate, calcium carbonate, lactose, sorbitol, mannitol, xylitol, sweeteners (e.g. sucrose, fructose, glucose, corn syrup, saccharides, saccharine, sucralose, aspartame, etc.), stearic acid, stearate, silica, silicate, flavors, and/or colors, among others.

Into ready-to-drink beverages with the addition of starch, modified starch, maltodextrin, cellulose, modified cellulose, protein hydrolysate, whey powder, calcium phosphate, calcium carbonate, lecithin, sweeteners (e.g. sucrose, fructose, glucose, corn syrup, saccharides, saccharine, sucralose, aspartame, etc.), sorbitol, mannitol, xylitol, silica, silicate, solvents (e.g. water, ethanol, polyethylene glycol, propylene glycol, glycerin), acidifiers (e.g. citric acid, acetic acid, malic acid, tartaric acid), citrate, preservatives (e.g. benzoic acid, benzoate, sorbic acid, sorbate, polysorbate, propionic acid, propionate, nisin), caffeine, flavors, and/or colors, among others.

Into semisolids such as gu with the addition of starch, modified starch, maltodextrin, cellulose, modified cellulose, protein hydrolysate, whey powder, calcium phosphate, calcium carbonate, lecithin, oil, partially hydrogenated oil, fat, milk, milk solids, mono- or diglycerides, polysorbates, sorbitan monostearate,(gum tragacanth, gum arabic, agar, guar gum, locust bean gum, karaya gum, xanthan gum, etc.), sweeteners (e.g. sucrose, fructose, glucose, corn syrup, saccharides, saccharine, sucralose, aspartame, etc.), sorbitol, mannitol, xylitol, silica, silicate, solvents (e.g. water, ethanol, polyethylene glycol, propylene glycol, glycerin), acidifiers (e.g. citric acid, acetic acid, malic acid, tartaric acid), citrate, preservatives (e.g. benzoic acid, benzoate, sorbic acid, sorbate, polysorbate, propionic acid, propionate, nisin, parabens), flavors, and/or colors, among others.

Into softgel capsules with the addition of lecithin, oil, wax, glycerine, gelatin, propylene glycol, polyethylene glycol, and/or colors, among others.

Into food or supplement bars with the addition of flour, starch, modified starch, maltodextrin, cellulose, methylcellulose, ethylcellulose, hydroxypropylmethylcellulose, modified cellulose, protein hydrolysate, whey powder, calcium phosphate, calcium carbonate, lecithin, mono- or diglycerides, polysorbates, sorbitan monostearate, binders (gum tragacanth, gum arabic, agar, guar gum, locust bean gum, karaya gum, xanthan gum, etc.), sweeteners (e.g. sucrose, fructose, glucose, corn syrup, saccharides, saccharine, sucralose, aspartame, etc.), sorbitol, mannitol, xylitol, silica, silicate, solvents (e.g. water, ethanol, polyethylene glycol, propylene glycol, glycerin), acidifiers (e.g. citric acid, acetic acid, malic acid, tartaric acid), citrate, preservatives (e.g. benzoic acid, benzoate, sorbic acid, sorbate, polysorbate, propionic acid, propionate, nisin, BHA, BHT, EDTA, TBHQ, etc.), flavors, and/or colors, among others.

Methods

Compositions of the present invention are taken by individuals experiencing a wide range of symptoms. Characteristics of such individuals include:

a) People who are experiencing one or more symptoms of an impending or fully established cold or flu, including joint pain, muscle aches, scratchy throat, fever, chills and stiff neck.

b) People who are or may be exposed to others experiencing the symptoms of a cold or flu.

c) People who wish to take preventative measures to reduce the likelihood of experiencing a cold or flu.

d) People who have depressed their immune system through exposure to cold weather, heightened physical exertion or other physical stresses such as physical work or exercise, sleeplessness or irregular sleep habits, emotional stress, prolonged illness, or immune function degradation that naturally occurs as part of the aging process.

e) People who want to strengthen their immune system against exposure to cold weather, heightened physical exertion or other physical stresses such as physical work or exercise, sleeplessness or irregular sleep habits, emotional stress, prolonged illness, or immune function degradation that naturally occurs as part of the aging process. People who want to support their body's ability to healthfully adapt to an environment or improve the resilience of their health to new, changing or challenging circumstances physically, emotionally, mentally.

f) People who are or may be exposed to others who may be contagious or could have an effect on the quality of their health or any circumstance that might effect the state of a person's health.

Typical individual consumption of the invention ranges from 450 mg to 1800 mg of a composition of the present invention once to three times per day, depending on the status of immune function and other factors such as exposure or activity levels.

Compositions of the present invention provide one with general well-being and improved resistance to illness. The expected benefits for a majority of those who are experiencing the early stage symptoms of a cold or flu are the reduction or cessation of one or more of the symptoms. Some may experience a reversal or cessation of all symptoms within 36 hours.

Kits

The various delivery systems for compositions of the present invention can be packaged in a number of ways as appropriate, including but not limited to:

Bottle with label and/or insert having instructions

Foil laminate pouch with instructions

Wrapper with instructions

Carton or box with instructions and/or label with instructions and/or insert with instructions For prevention, Adults take 450 mg-900 mg of the formulation once a day, one to two weeks on and two or three days to one week off. At the first indication of the symptoms of cold or flu, Adults take 900 to 1800 mg of the blend every 4 to 8 hours until symptoms are reduced. If you are taking a prescription medication or are pregnant or lactating, consult with you doctor before taking the formulation.

Experimental Results

EXAMPLE 1

Numerous subjects tested using the BioRim™ medium (i.e., *Eleuthero, Stephani, Epimedium* composition of the present invention) throughput method showed marked improvement in immune response to cold and flu. The same subjects were tested using control, placebo and the formulation (ESE) and the individual ingredients. The ingredients individually had little to no effect in strengthening the subjects' immune systems. The formulation of the three combined ingredients showed a significant increase in immune response in all subjects.

The invention claimed is:

1. A method for treating a common cold in a subject in need thereof, wherein the method comprises administration of a composition, and wherein the composition consists essentially of: 2 weight percent to 95 weight percent *Eleuthero;* 2 weight percent to 95 weight percent *Stephania;* and, 2 weight percent to 95 weight percent *Epimedium.*

2. The method according to claim 1, wherein the composition consists essentially of: 5 weight percent, 10 weight percent, 15 weight percent or 20 weight percent *Eleuthero;* 90 weight percent, 85 weight percent, 80 weight percent or 75 percent *Stephania;* and, 20 weight percent, 15 weight percent, 10 weight percent or 5 weight percent *Epimedium.*

3. The method according to claim 1, wherein the composition consists essentially of: 25 weight percent, 30 weight percent, 35 weight percent or 40 weight percent *Eleuthero;* 70 weight percent, 65 weight percent, 60 weight percent or 55 weight percent *Stephania;* and, 20 weight percent, 15 weight percent, 10 weight percent or 5 weight percent *Epimedium.*

4. The method according to claim 1, wherein the composition consists essentially of: 5 weight percent, 10 weight percent, 15 weight percent or 20 weight percent *Eleuthero;* 20 weight percent, 15 weight percent, 10 weight percent or 5 weight percent *Stephania;* and, 90 weight percent, 85 weight percent, 80 weight percent or 75 weight percent *Epimedium.*

5. The method according to claim 1, wherein the composition consists essentially of: 25 weight percent, 30 weight percent, 35 weight percent or 40 weight percent *Eleuthero;* 20 weight percent, 15 weight percent, 10 weight percent or 5 weight percent *Stephania;* and, 70 weight percent, 65 weight percent, 60 weight percent or 55 weight percent *Epimedium.*

6. The method according to claim 1, wherein the composition consists essentially of 45 weight percent, 50 weight percent, 55 weight percent or 60 weight percent *Eleuthero;* 50 weight percent, 45 weight percent, 40 weight percent or 35 weight percent *Stephania;* and, 20 weight percent, 15 weight percent, 10 weight percent or 5 weight percent *Epimedium.*

7. The method according to claim 1, wherein the composition consists essentially of 45 weight percent, 50 weight percent, 55 weight percent or 60 weight percent *Eleuthero;* 20 weight percent, 15 weight percent, 10 weight percent or 5 weight percent *Stephania;* and, 50 weight percent, 45 weight percent, 40 weight percent or 35 weight percent *Epimedium.*

8. The method according to claim 1, wherein the composition consists essentially of 65 weight percent, 70 weight percent, 75 weight percent or 80 weight percent *Eleuthero;* 30 weight percent, 25 weight percent, 20 weight percent or 15 weight percent *Stephania;* and, 20 weight percent, 15 weight percent, 10 weight percent or 5 weight percent *Epimedium.*

9. The method according to claim 1, wherein the composition consists essentially of 25 weight percent, 30 weight percent, 35 weight percent or 40 percent *Eleuthero;* 40 weight percent, 35 weight percent, 30 weight percent, 25 weight percent or 20 weight percent *Stephania;* and, 55 weight percent, 50 weight percent, 45 weight percent, 40 weight percent, 35 weight percent, 30 weight percent, or 25 weight percent *Epimedium.*

* * * * *